United States Patent [19]
Löhn

[11] Patent Number: 4,886,452
[45] Date of Patent: Dec. 12, 1989

[54] DENTAL SPRAY HANDPIECE

[75] Inventor: Gerd Löhn, Biberach/Rissegg, Fed. Rep. of Germany

[73] Assignee: Kaltenbach & Voigt GmbH & Co., Biberach/Riss, Fed. Rep. of Germany

[21] Appl. No.: 249,724

[22] Filed: Sep. 27, 1988

[30] Foreign Application Priority Data

Oct. 14, 1987 [DE] Fed. Rep. of Germany ....... 3734864

[51] Int. Cl.⁴ .................. A61D 3/00; A61G 17/02
[52] U.S. Cl. ..................................... 433/32; 433/80
[58] Field of Search .............. 433/80, 81, 85, 88, 433/29, 32

[56] References Cited

U.S. PATENT DOCUMENTS

| | | | |
|---|---|---|---|
| 3,831,815 | 8/1974 | Glasgow | 433/32 |
| 4,249,899 | 2/1981 | Davis | 433/32 |
| 4,531,912 | 7/1985 | Schuss et al. | 433/32 |
| 4,619,612 | 10/1986 | Weber et al. | 433/80 |

FOREIGN PATENT DOCUMENTS

| | | | |
|---|---|---|---|
| 1227187 | 10/1966 | Fed. Rep. of Germany | 433/85 |
| 2239346 | 2/1973 | Fed. Rep. of Germany | . |
| 2702968 | 7/1978 | Fed. Rep. of Germany | . |
| 2920009 | 11/1980 | Fed. Rep. of Germany | 433/32 |
| 2930228 | 2/1981 | Fed. Rep. of Germany | . |

Primary Examiner—John J. Wilson
Attorney, Agent, or Firm—Scully, Scott, Murphy & Presser

[57] ABSTRACT

A dental spray handpiece, consisting of a gripping sleeve having a media inlet connection at one end thereof and a media discharge at the other end. In the sleeve there are arranged two media conduits extending from the media inlet connection to the media discharge and discharging outwardly therefrom, of which one conduit is connected to a source of air and the other to a source of water, each of the two media conduits having associated therewith a respective electrical heating device with an associated heating current circuit for the heating of the medium.

18 Claims, 2 Drawing Sheets

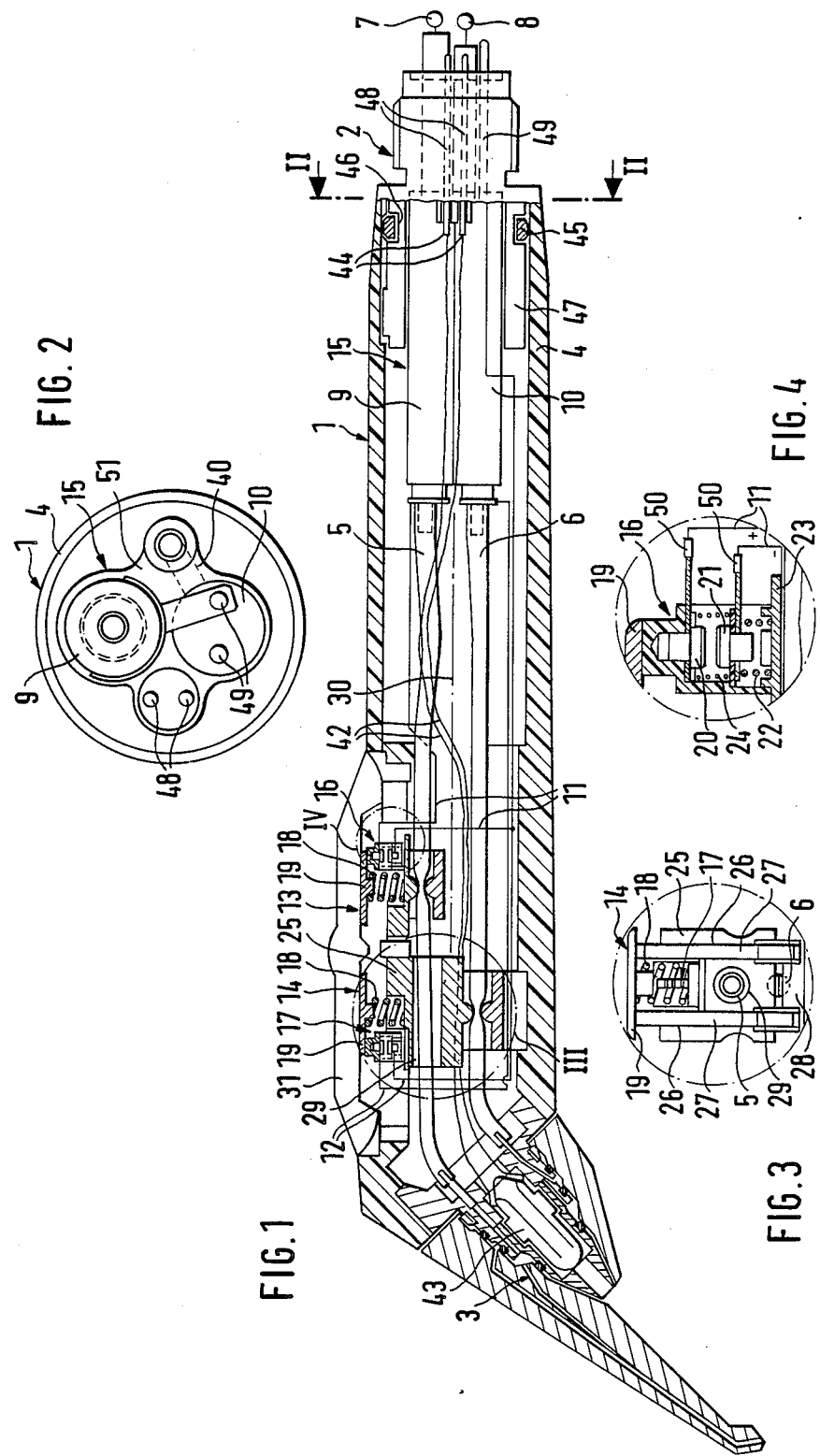

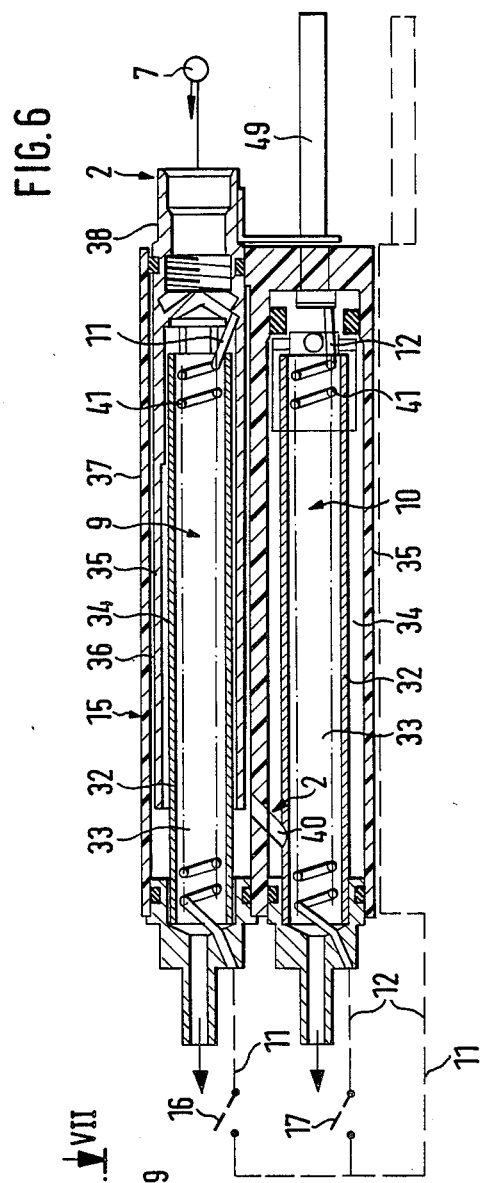
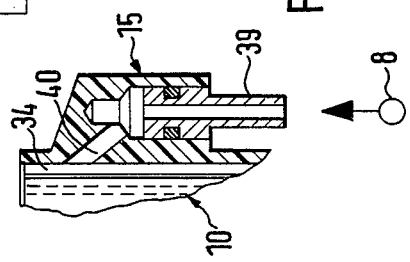
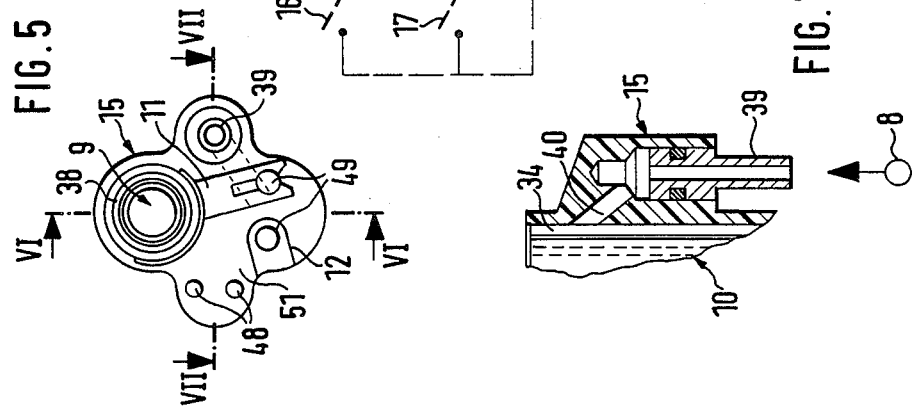

DENTAL SPRAY HANDPIECE

BACKGROUND OF THE INVENTION

1. Field of the Invention

The present invention relates to a dental spray handpiece, consisting of a gripping sleeve having a media inlet connection at one end thereof and a media discharge at the other end, in which there are arranged two media conduits extending from the media inlet connection to the media discharge and discharging outwardly therefrom, of which one conduit is connected to a source of air and the other to a source of water, each of the two media conduits having associated therewith a respective electrical heating device with an associated heating current circuit for the heating of the medium.

2. Discussion of the Prior Art

A spray handpiece of this type has become known from the disclosures of German Laid-Open Patent Appln. 29 20 009 or German Laid-Open Patent Application 32 08 666. In this known spray handpiece, the electrical heating devices are permanently built into the gripping sleeve. The consequence of this permanent installation is that it renders the servicing of the heating devices more difficult, and does not allow for an exchange of the latter.

SUMMARY OF THE INVENTION

The present invention provides for a dental spray handpiece of the type as considered herein, in which the electrical heating devices form a unitary structure which is detachably inserted into the gripping sleeve, so as to thereby facilitate a simple servicing of the heating devices, as well as an exchange of the heating devices which can be carried out in a simple manner.

The advantages which are obtained through the intermediary of the present invention can be essentially ascertained in that the two heating devices are commonly, in essence, together as a unitary structure, simply and rapidly removed from the gripping sleeve, serviced in this disassembled condition, and thereafter again to be able to rapidly and simply be inserted into the gripping sleeve; and just as rapidly and simply, in case of need, is it possible to effect an exchange of the two heating devices which are combined into a unitary structure.

BRIEF DESCRIPTION OF THE DRAWINGS

Advantageous modifications and features of the invention can now be be readily ascertained from the following detailed description of exemplary embodiments thereof, taken in conjunction with the accompanying drawings; in which:

FIG. 1 illustrates, a longitudinal sectional view through the inventive dental spray handpiece;

FIG. 2 illustrates on an enlarged scale a sectional view taken along line II—II in FIG. 1;

FIG. 3 illustrates a cross-sectional view of a shutoff valve for the encircled portion III in FIG. 1, which represents a media conduit formed by a water line;

FIG. 4 illustrates, on an enlarged scale, an on-off switch for a heating current circuit represented by the encircled portion IV in FIG. 1;

FIG. 5 illustrates the unitary structure encompassing the two heating devices, shown in a view towards the end distant from the gripping sleeve;

FIG. 6 illustrates a sectional view taken along line VI—VI in FIG. 5; and

FIG. 7 illustrates a sectional view taken along line VII—VII in FIG. 5.

DETAILED DESCRIPTION

The illustrated dental spray handpiece 1 consists of a gripping sleeve 4 possessing a media connection 2 at one end thereof and a media discharge 3 at the other end. In the gripping sleeve 4 there are arranged two media conduits 5, 6 which extend from the media inlet connection to the media discharge and discharge outwardly therefrom, of which one conduit is connected to an source of air 7 and the other conduit to a source of water 8. The two media conduits 5, 6 are each provided with a respective electrical heating device 9, 10 for heating the medium, including an associated heating current circuit 11, 12.

The electrical heating devices 9, 10 form a unitary structure possessing a common housing 51, which is removably inserted into the gripping sleeve 4.

In each of the current circuits 11, 12 for the heating devices 9, 10 there is respectively arranged an on-off switch 16, 17. The two media conduits 5, 6 each have a shutoff valve 13, 14 associated therewith, which is bringable into the open position through finger-actuation, whereby the on-off switches 16, 17 are functionally combined with the shutoff valves 13, 14 either structurally and/or functionally to provide for common actuation.

In specific detail, the construction is such that the shutoff valves 13, 14 are each provided with a pushbutton which is depressable against the action of a first return spring 18 from a closed position into an open position, whereby presently one contact element 20 of two contact elements 20, 21 of the on-off switch 16, 17 which come into contact with each other upon depression of the pushbutton 19, under side of the pushbutton 19.

The second contact element 21 can be arranged fixed in position in the gripping sleeve 4; however, as illustrated by means of a second return spring 22 it can also be supported against a part 23 which is fixedly arranged in the gripping sleeve. The contact element 20 which cooperates with the underside of the pushbutton 19, lies against the underside of the pushbutton 19 under the action of a third return spring 25.

The media conduits 5, 6, or presently at least a portion thereof, are constituted from an elastic material, whereby the shutoff valves 13, 14 are formed as squeeze valves acting on the elastic material, in which the first return spring 18 is supported against a bearing block 25 which is fixedly located within the gripping sleeve 4; with the bearing block possessing two bores 26 through which there extend two guide rods 27 which are connected with the pushbutton 19. At their free ends, the guide rods are interconnected by a squeeze element 28 which, in the closed position, clamps one of the elastic media conduits 5 or 6 or their elastic portion between itself and the bearing block 25 under the action of the first return spring 18. As illustrated in FIGS. 1 and 2, the bearing block 25 is provided with a breakthrough 29 for the through-passage of the other media conduit 6 or 5.

The shutoff valves 13, 14 are arranged behind each other in parallel lines relative to the longitudinal axis 30 of the gripping sleeve 4, whereby the pushbuttons 19 for the shutoff valves 13, 14 are covered by an elastic covering 31. The covering 31 can be taken off in a simple manner, such that after removal of the pushbuttons 19, the on-off switches 16, 19 for the electrical heating devices 9, 10 become easily accessible.

With respect to the configuring of the electrical heating devices 9, 10 which are combined into a unitary structure 15, the construction is, in detail, such that the electrical heating devices 9, 10 are each presently arranged within a heating tube 32 which connected into the media conduits 5, 6, which, under the formation of an annular gap 34 at its end which is in communication with the interior space of the heating tube 33, is encompassed by a mantle or jacket tube 35.

In the electrical heating device 9 for air, pursuant to FIG. 6, the jacket tube 35 which forms an intermediate tube, under the formation of an outer annular gap 34 which is at one end thereof in communication with the mentioned annular gap 34, is encompass by separate outer tube 37, which is in communication with the media inlet connection 2.

With regard to the electrical heating device 10 for water, the jacket tube 35 is an external tube, which is in connection with the media inlet connection 2.

As can be ascertained in particular from FIG. 6, the heating device 9 which possesses the separate outer tube 37 is associated with the media conduit 5 conveying the air, whereas the heating device 10 possessing the jacket tube 35 which is only formed by an outer tube is associated with the media conduit 6 conveying the water.

The outer annular gap 36 bounding the separate outer tube 37 is in communication with the air source 7 through an air-inlet connector 38, whereas the annular gap 34 which is bounded by the jacket tube 35 is in communication with the water source 8 through a radial passageway 40 and a water-inlet connector 39.

FIG. 6 further illustrates that the electrical heating devices 9, 10 each incorporate heating coils 41 which are arranged in the interior space 33 of the heating tube 32.

From FIG. 1 there can be ascertained that an electrical current circuit 42 for light for the operation of an incandescent lamp or lightbulb 43 which emits light from the media discharge 3 is provided in the gripping sleeve 4, whereby the light-current circuit 42 is in communication through electrical socket plug connectors 44 with the media inlet connection 2 which is connected with the unitary structure 15. This embodiment, with respect to the incandescent lamp 43, also serves for the easier detachability of the unitary structure 15 from the gripping sleeve 4. For the same reason are the media conduits 5, 6 in connection by means of media socket plug connectors 45 with the unitary structure 15. The heating-current circuits 11, 12 also possess electrical socket plug connector; for example, elements 50, for connection with the on-off switches 16, 17.

As illustrated in FIG. 1, the unitary structure 15 which carries the media inlet connection 2, possesses an external clamping ring 45 producing a clamping seat for detachable insertion into the gripping sleeve 4. This configuration also facilitates the easy installation and disassembly of the unitary structure 15. Thereby, the clamping ring 45 is arranged in an external annular groove 46 in a coupling sleeve 47 supporting the media inlet connection 2, and which encompasses the unitary structure.

From FIGS. 1 and 5 there can be further ascertained that the media inlet connection 2; in effect, the unitary structure 15, is additionally provided on the side distant from the gripping sleeve, besides the media supplyplug connections which are formed by the socket plug connectors 38, 39, with socket plug connectors 48 for the light-current supply and socket plug connectors 49 for the heating-current supply.

Instead of being angled or bent as shown in FIG. 1, the end section of the gripping sleeve 4 towards the media discharge can also extend straight.

What is claimed is:

1. Dental spray handpiece, consisting of a gripping sleeve having a media inlet connection at one end thereof and a media discharge at another end; to media conduits extending through said gripping sleeve from the media inlet connection to the media discharge and discharging outwardly therefrom, one said conduit being connected to a source of air and the other said conduit being connected to a source of water; electrical heating means with associated electrical current circuits for heating the media being associated with each of said two media conduits, said electrical heating means constituting a unitary structure which is detachably inserted into said gripping sleeve, said electrical heating means each being arranged in a heating tube connected with the media conduits, said tube being encompassed by a jacket tube with the formation of an annular gap at one end thereof communicating with the interior space of the heating tube, said jacket tube including an intermediate tube with the formation of an outer annular gap at the end thereof which is in communication with said inner annular gap; and a separate outer tube encompassing said jacket tube which is in communication with the media inlet connection.

2. Spray handpiece as claimed in claim 1, wherein a shutoff valve is operatively associated with respectively each of said two media conduits, each said valve including a pushbutton for directly bringing said valve into an open position opposite a spring pressure through finger-actuation on said pushbutton.

3. Spray handpiece as claimed in claim 2, wherein a first return spring is interposed between each said shutoff valve and pushbutton.

4. Spray handpiece as claimed in claim 3, wherein at least a portion of each of the media conduits in the region of the shutoff valves is constituted of an elastic material, aid shutoff valves comprising squeeze valves acting on the elastic material, said first return spring being supported against a bearing block fixedly arranged within the gripping sleeve, said bearing block having two bores, two guide rods extending through the bores which are connected with the pushbutton, the free ends of said rods being interconnected through a squeezing element which, in the closed position, clamps the elastic portion between itself and said bearing block under the biasing action of the first return spring.

5. Spray hand piece as claimed in claim 4, wherein said bearing block includes a breakthrough for the through-passage of the other media conduit.

6. Spray handpiece as claimed in claim 3, wherein a second of said contact elements is fixedly arranged within the gripping sleeve.

7. Spray handpiece as claimed in claim 6, wherein said second contact element is supported by a second return spring against an element which is fixedly arranged within the gripping sleeve.

8. Spray handpiece as claimed in claim 3, wherein the contact element cooperating with the underside of the pushbutton contacts against the underside of the pushbutton under the biasing action of a third return spring.

9. Spray handpiece as claimed in claim 2, wherein said shutoff valves are arranged behind each other along a parallel line relative to the longitudinal axis of said gripping sleeve.

10. Spray handpiece as claimed in claim 1, wherein the pushbuttons for said shutoff valves are covered by an elastic covering.

11. Spray handpiece as claimed in claim 1, wherein said jacket tube is an outer tube which is in communication with the media inlet connection.

12. Spray handpiece as claimed in claim 11, wherein the heating means possessing the jacket tube which is formed only by an outer tube is associated with the media conduit conveying water.

13. Spray handpiece as claimed in claim 12, wherein the annular gap bounded by the jacket tube is in connection through a radial passageway and a water-inlet connector with the source of water.

14. Spray handpiece as claimed in claim 1, wherein the heating means possessing the separate outer tube is associated with the media conduit conveying air.

15. Spray handpiece as claimed in claim 14, the outer annular gap bounded by the separate outer tube is connected with the source of air through an airinlet connector.

16. Spray handpiece as claimed in claim 1, wherein the electrical devices each include a heating coil arranged in the interior space of the heating tube.

17. Spray handpiece as claimed in claim 1, wherein the unitary structure supporting the media inlet connection includes an external clamping ring forming a clamping seat for detachable insertion into said gripping sleeve.

18. Spray handpiece as claimed in claim 17, wherein said clamping ring is arranged in an external annular groove in a coupling sleeve supporting the media inlet connection and encompassing the unitary structure.

* * * * *